United States Patent
Talbot et al.

(10) Patent No.: US 10,788,142 B2
(45) Date of Patent: Sep. 29, 2020

(54) BLOCKING MECHANISM FOR A STOPCOCK MANIFOLD

(71) Applicant: Trasis S.A., Ans (BE)

(72) Inventors: Ludovic Talbot, Andrimont (BE); Frederic Baplue, Fraiture (BE); Jean-Luc Morelle, Liege (BE)

(73) Assignee: TRASIS S.A., Liege (BE)

( * ) Notice: Subject to any disclaimer, the term of this patent is extended or adjusted under 35 U.S.C. 154(b) by 0 days.

(21) Appl. No.: 16/093,144

(22) PCT Filed: Mar. 9, 2017

(86) PCT No.: PCT/EP2017/055555
§ 371 (c)(1),
(2) Date: Oct. 12, 2018

(87) PCT Pub. No.: WO2017/178156
PCT Pub. Date: Oct. 19, 2017

(65) Prior Publication Data
US 2019/0338864 A1    Nov. 7, 2019

(30) Foreign Application Priority Data

Apr. 15, 2016  (EP) .................................. 16165515
Jun. 10, 2016  (BE) .................................. 2016/5436

(51) Int. Cl.
*F16K 31/52*    (2006.01)
*F16K 5/04*     (2006.01)
*F16K 11/22*    (2006.01)

(52) U.S. Cl.
CPC .............. *F16K 31/522* (2013.01); *F16K 5/04* (2013.01); *F16K 11/22* (2013.01)

(58) Field of Classification Search
CPC ........ F16K 27/003; F16K 31/522; F16L 3/11; F16L 3/1091; A61M 5/1408; A61M 2039/1016
See application file for complete search history.

(56) References Cited

U.S. PATENT DOCUMENTS 3,477,469 A    11/1969  Paleyhyman
4,432,392 A    2/1984   Paley
(Continued)

FOREIGN PATENT DOCUMENTS

EP    0637712 A1    2/1995
EP    1602388 A1    12/2005

*Primary Examiner* — Angelisa L. Hicks
(74) *Attorney, Agent, or Firm* — Leydig, Voit & Mayer, Ltd.

(57) ABSTRACT

A stopcock manifold system includes: a manifold provided with one or several stopcocks, each having a rotary opening/closing control apparatus with at least one finger or crank pin; a rotary mechanized actuator coupling part for each manifold, a rotary axis of the coupling part corresponding in use to a rotation axis of the control apparatus, the coupling part coupling with the stopcock by insertion of each crank pin into a closed notch in the coupling part, the closed notch of each coupling part receiving one of the crank pins of the corresponding stopcock, such that the crank pin is insertable into the corresponding coupling part by tilting the manifold and then straightening it, until it abuts on a first bearing point comprised of an edge of the closed notch; and a maintaining system that enables each coupling part to individually maintain the corresponding stopcock in place.

7 Claims, 6 Drawing Sheets

(56) References Cited

U.S. PATENT DOCUMENTS

| | | |
|---|---|---|
| 4,447,236 A | 5/1984 | Quinn |
| 5,460,204 A | 10/1995 | Rossi |
| 6,099,511 A | 8/2000 | Devos et al. |
| 2003/0030021 A1* | 2/2003 | Hawkins ............. F15B 13/0817 251/291 |
| 2007/0142197 A1* | 6/2007 | Marsh ................... G01F 11/284 494/10 |
| 2011/0011474 A1 | 1/2011 | Duncan |

* cited by examiner

BLOCKING MECHANISM FOR A STOPCOCK MANIFOLD

CROSS-REFERENCE TO PRIOR APPLICATIONS

This application is a U.S. National Phase application under 35 U.S.C. § 371 of International Application No. PCT/EP2017/055555, filed on Mar. 9, 2017, and claims benefit to European Patent Application No. EP 16165515.4, filed on Apr. 15, 2016, and Belgian Patent Application No. BE 2016/5436, filed on Jun. 10, 2016. The International Application was published in French on Oct. 19, 2017 as WO 2017/178156 under PCT Article 21(2).

FIELD

The present invention relates to a mechanism for maintaining or blocking a stopcock manifold or individual stopcocks on mechanized actuator couplings, for example rotary, which may or may not be automated.

BACKGROUND

Definitions

A stopcock valve manifold refers to a component, made from any material, made up of a manifold body provided with inlet/outlet couplings for liquid or gas fluid, in which one or several stopcocks are included. This type of component is often designed to be used only once.

In particular, this component allows, subject to a manual or automated actuation of the stopcock(s), to manage the flows of liquids and/or gases in the context of manipulations generally associated with the pharmaceutical and medical fields.

Figure 1A:
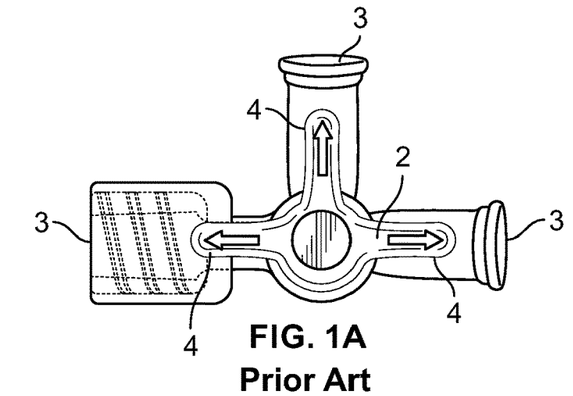
FIGS. 1A-B illustrate examples of a stopcock and a stopcock manifold according to the state of the art.
Figure 1B:
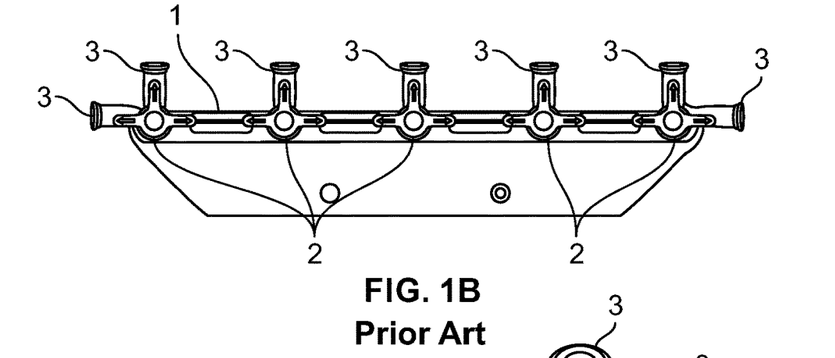
Figure 2:
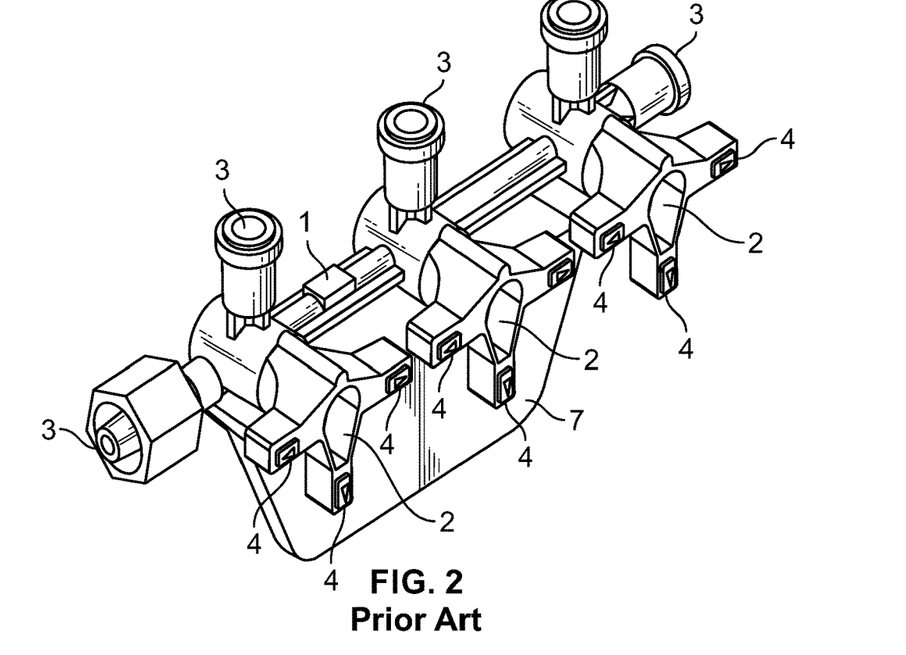
FIG. 2 illustrates another example of a stopcock manifold according to the state of the art.
Figure 3A:
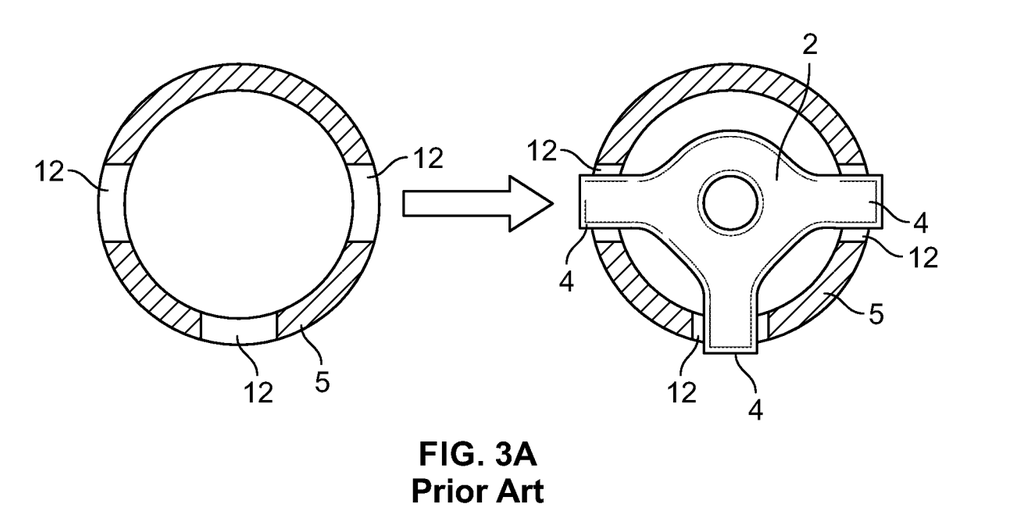
FIGS. 3A-B show the general principle of a coupling with open notches, according to the state of the art, and inserting the stopcock fingers of a stopcock into the open notches.
Figure 3B:
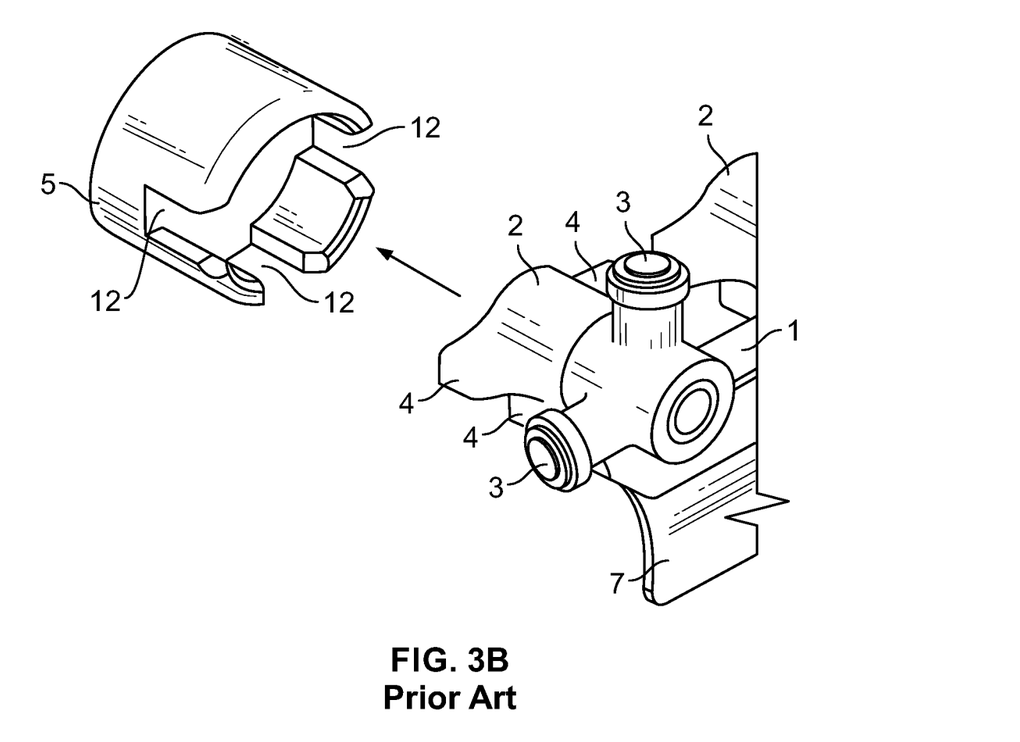

Examples are shown in FIGS. 1 and 2. In particular, FIG. 2 shows a stopcock valve manifold body 1 with inlet/outlet couplings 3, on which three stopcock valves 2 are mounted, each having at least one stopcock valve finger or crank pin 4 (in the case at hand, three). See for example www.nordsonmedical.com, US 2011/0011474 A1, etc.

Technological background and problem to be solved

Automated or non-automated, mechanized actuating devices for stopcock valve manifolds have been marketed in various fields, in particular in radio-pharmaceutical chemistry, in order to:

protect the operator from potential risks, for example when certain fluids are radioactive;
facilitate the operator's task, the stopcocks being actuated by motors or jacks;
secure methods that may include complex actuating sequences.

Irrespective of the field of application, the principle consists of coupling the stopcocks with rotary actuators, by means of coupling parts adapted to the shape of the crank pins of the stopcocks that are used to transmit the rotating movement to the stopcock.

Whether the stopcock valve manifold is placed horizontally or vertically, it does not spontaneously assume its position in the couplings due to gravitational forces and movements transmitted to the stopcocks by the couplings during their actuation. It should therefore be kept in place using any appropriate device.

The stopcock valve manifolds are of various commercial origins and have variable shapes and sizes. No universal fastening/blocking mechanism is therefore known.

Figure 4A:
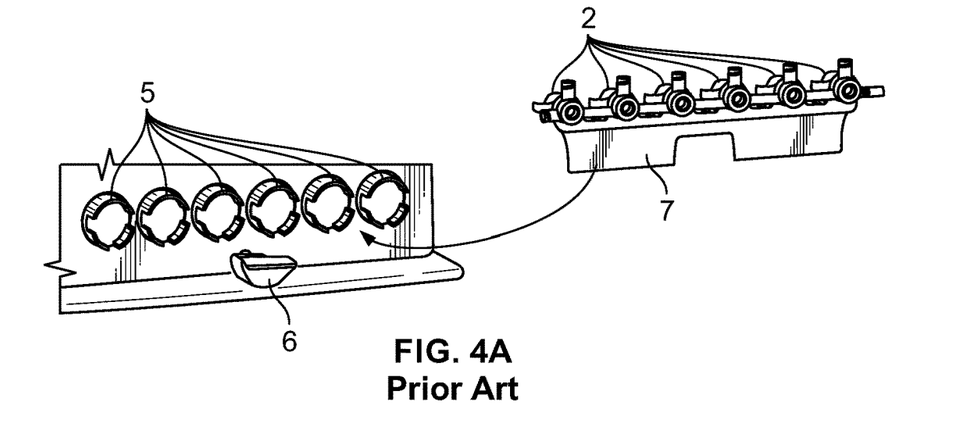
FIGS. 4A-C show the different steps of the coupling of the stopcock fingers of the stopcocks with open notches, according to the state of the art.
Figure 4B:
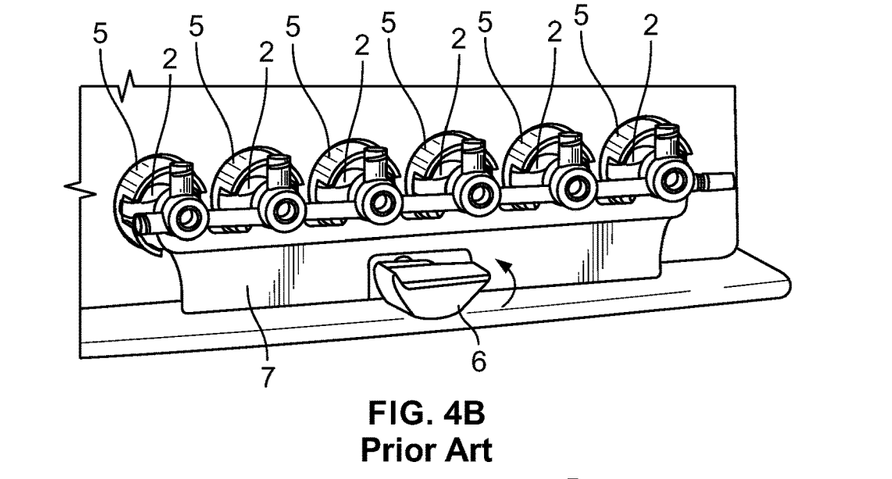
Figure 4C:
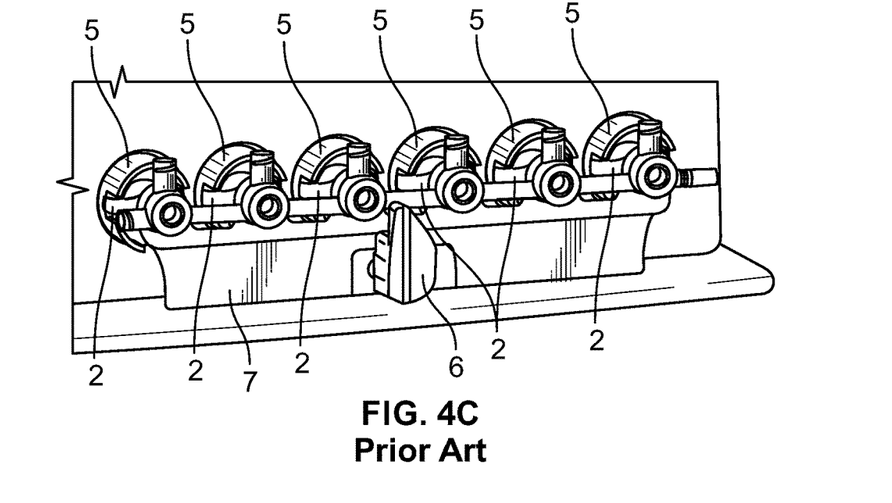

As shown in FIGS. 3A-B and 4A-C, one typically-adopted solution consists in inserting the stopcocks 2 into rotary couplings with open notches 5 (with or without centering) and in maintaining the stopcock valve manifold 7 in the notches using a latch 6 that is manually or automatically actuated and maintains the manifold as a whole. FIGS. 4A-C respectively show the steps for inserting (FIG. 4A) the stopcock valve manifold 7 into the couplings with open notches 5, actuating the latch 6 (FIG. 4B) and obtaining the blocked position of the manifold (FIG. 4C).

The operator must therefore position the stopcock valve manifold in two steps:
  inserting the stopcock valve manifold into the actuator couplings and keeping it there;
  actuating the maintaining or blocking mechanism.

Thus, the stopcocks are not directly maintained by the couplings themselves, but by means of the parts for maintaining the whole manifold, which are often cumbersome and do not always provide an absolute guarantee that each manifold crank pin is inserted into its coupling.

For the stopcock valve manifolds mounted on the devices marketed in the pharmaceutical and medical fields, there are often bearing points located at the front of the stopcock valve manifold, such as wheels, allowing blocking in the direction of the axis of the stopcocks. The maintaining mechanism is often made up of a movable plate that can either move along the axis of the stopcocks, or be pivotingly retractable.

Figure 5:
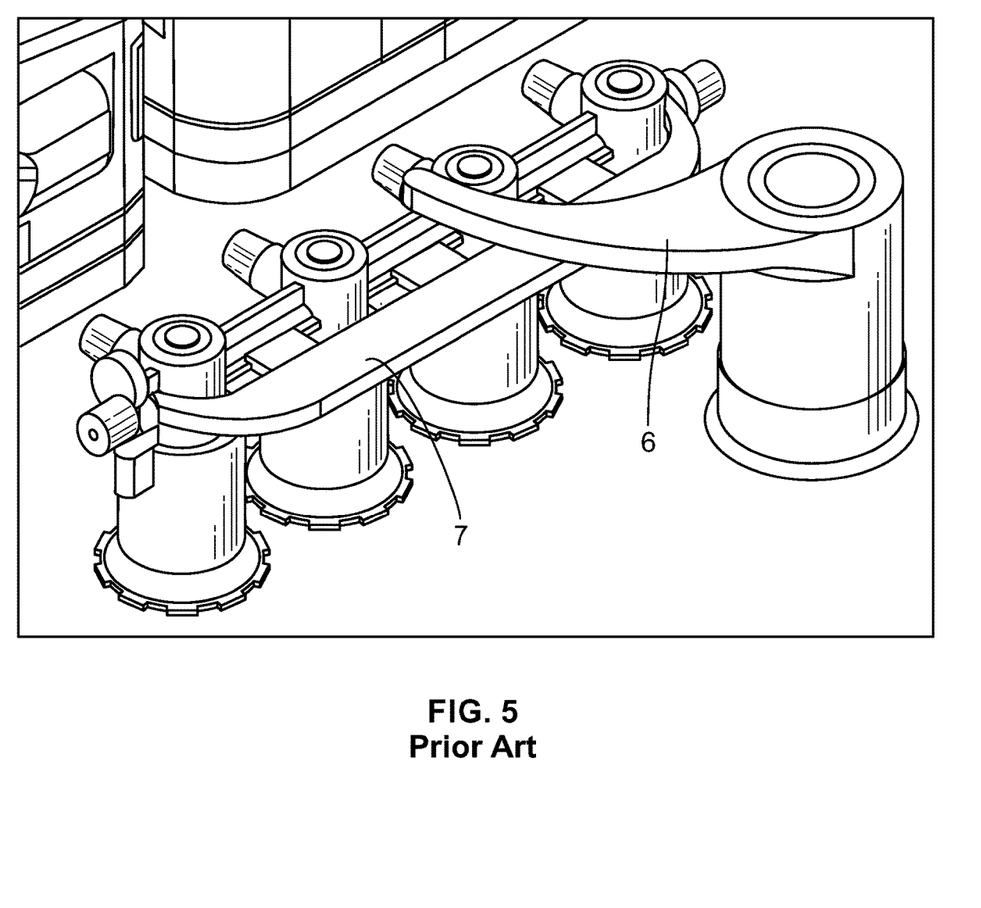
FIG. 5 shows an example mechanism for maintaining a stopcock manifold according to the state of the art, by means of a part for maintaining the manifold as a whole.
Figure 6A:
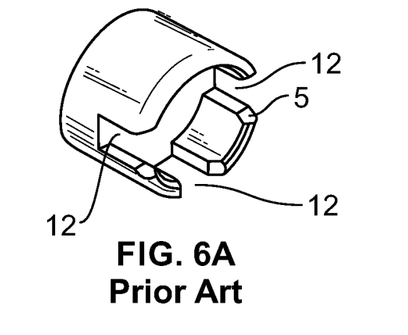
FIGS. 6A-E contrast the general principle of a coupling with closed notches, according to one embodiment of the present invention, as shown in FIGS. 6B-E, with the general principle of a coupling with open notches, according to the state of the art, as shown in FIG. 6A.
Figure 6B:
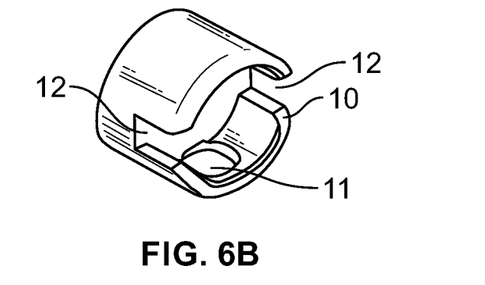
Figure 6C:
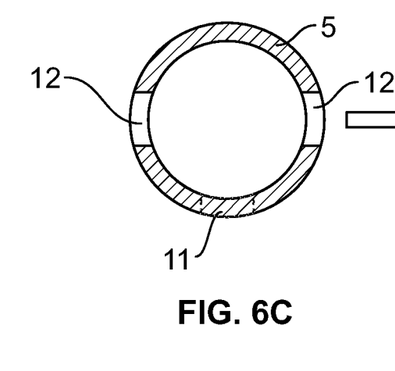
Figure 6D:
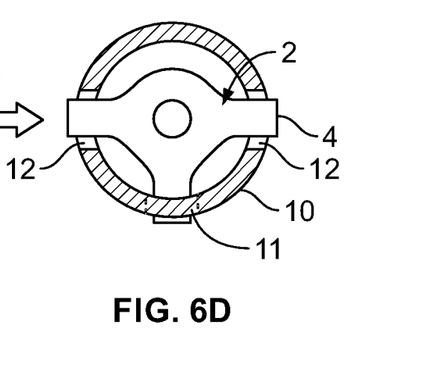
Figure 6E:
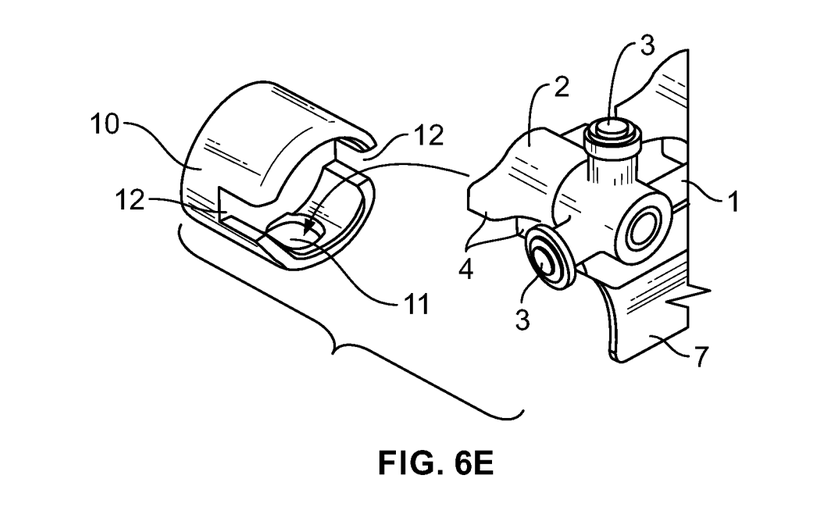

Another example of maintaining mechanism, shown in FIG. 5, is mounted on a device marketed by the applicant (TRASIS UniDose™).

SUMMARY

In an embodiment, the present invention provides a stopcock manifold system, comprising: a manifold provided with one or several stopcocks, each having a rotary opening/closing control apparatus with at least one finger or crank pin; a rotary mechanized actuator coupling part for each manifold, a rotary axis of the coupling part corresponding in use to a rotation axis of the control apparatus, the coupling part coupling with the stopcock by insertion of each crank pin into a closed notch in the coupling part, the closed notch of each coupling part being configured to receive one of the crank pins of the corresponding stopcock, such that the crank pin is insertable into the corresponding coupling part by tilting the manifold and then straightening it, until it abuts on a first bearing point comprised of an edge of the closed notch; a maintaining system configured such that each coupling part individually maintains the corresponding stopcock in place; and a latch configured to maintain the manifold as a whole in this straightened position, by pressing one end of the latch on the manifold, defining a second bearing point.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

In an embodiment, the present invention provides a device that allows to overcome the drawbacks of the state of the art.

In particular, in an embodiment, the invention guarantees easy positioning of a stopcock valve manifold and allows the reliable maintaining or blocking of said manifold in the usage position.

In an embodiment, the invention further provides an original solution for maintaining a stopcock valve manifold in place, directly integrated into the couplings themselves.

In an embodiment, the invention further provides a mechanism where each coupling maintains its own manifold.

The present invention relates to a stopcock manifold system, comprising a manifold provided with one or several stopcocks, each having a rotary control apparatus for opening/closing with at least one finger or crank pin, a rotary mechanized actuator coupling part for each manifold, the rotary axis of said coupling part corresponding in use to the rotation axis of said control apparatus, the coupling with the stopcock being produced by inserting each crank pin into a notch made in said coupling part and a maintaining system designed so that each coupling part individually maintains the corresponding stopcock in place, characterized in that:
  the coupling part comprises a closed notch, made to receive one of the crank pins of the corresponding stopcock, such that this crank pin can be inserted into the corresponding coupling part by tilting the manifold (forward) and then straightening it, until it abuts on a first bearing point, called front bearing point, aligned with the closed notch;
  a latch allows to maintain the manifold as a whole in this straightened position, by pressing one end of said latch on the manifold, defining a second bearing point, called rear bearing point.

It will be noted that, in the configuration of the invention, the normal usage position of the stopcock valve manifold is the vertical position, i.e., corresponding to a vertical flow. The "front" position of the manifold designates a proximal position of the device, and the "rear" position of the manifold designates a distal position of the device.

Thus, according to the invention, one of the open notches of the coupling parts, commonly used in the state of the art, is replaced by a closed notch. According to the invention, once the crank pin is obliquely inserted into this closed notch, the edge of the notch serves as a stop and will prevent, near the device, any return movement of the crank pin moving away from the device ("front" stop). The other bearing point will be the end of the latch that pushes on a rear part of the manifold ("rear" stop), which prevents, at a distance from the device, any movement of the manifold approaching the device. Since the two bearing points are located in separate and opposite positions, no torque can tilt/pivot the manifold any longer, making its withdrawal impossible in that state.

According to preferred embodiments of the invention, the stopcock valve manifold system further comprises one of the following features, or a suitable combination of several thereof:
  the latch is a passive latch, of the spring type;
  the spring latch is a tongue designed to move away from its equilibrium point when the manifold, while obliquely inserting into the closed notches of the coupling parts, simultaneously pushes on the aforementioned end of the latch, and to return to its equilibrium point once the manifold has been straightened, while blocking the manifold by abutting at the level of its rear bearing point;
  the latch is an active or automated latch;
  the latch comprises a sensor for detecting the position of the manifold and an actuator triggering a push-piece when the sensor detects the straightened position of the manifold.

The invention consists in implementing a principle for maintaining stopcock valve manifolds on the actuating mechanism in which the manifolds are maintained individually in their coupling. The stopcock valve manifold are positioned in one simple movement.

Figure 7A:
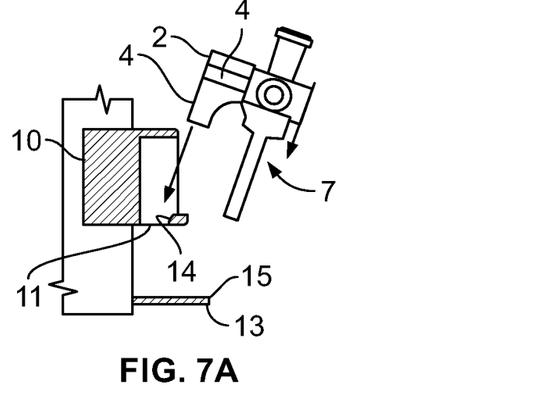
FIGS. 7A-E show the different steps of the coupling with closed notches and spring latch, according to one embodiment of the present invention.
Figure 7B:
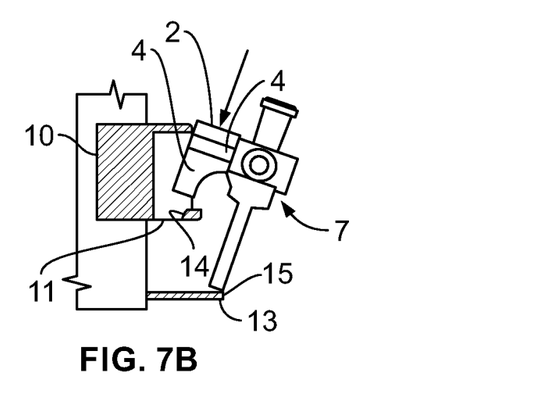
Figure 7C:
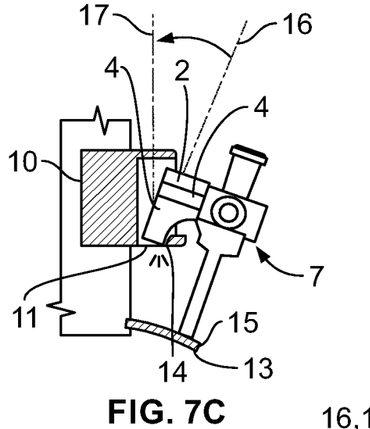
Figure 7D:
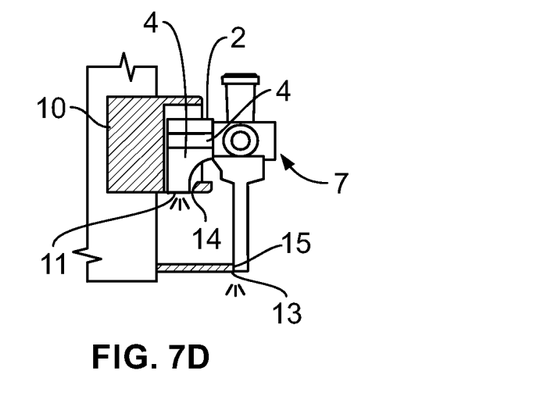
Figure 7E:
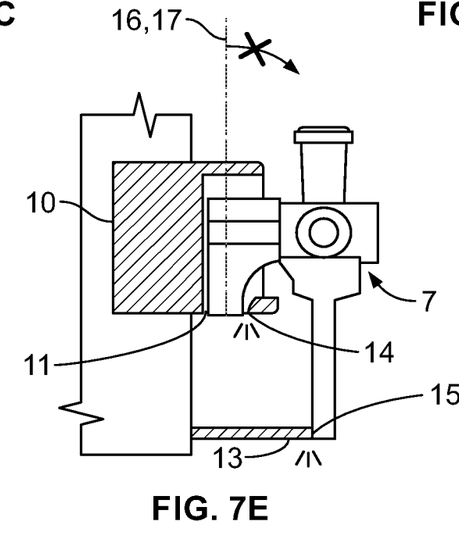

The device consists of the following combination of elements (FIGS. 6B-E, and 7A-E):
  one of the open notches 12 of the coupling part 10 is replaced by a closed hole 11. As the manifold is positioned, one of the fingers 4 of each stopcock 2 is inserted into this hole 11. The manifold is brought obliquely closer to allow the insertion, as shown in FIGS. 6E and 7A-D. Once the stopcock 2 is inserted into the coupling 10, the manifold 7 is tilted such that the rotation axis 16 of the stopcock 2 and the vertical axis 17 of the coupling 10 are aligned, as shown in FIGS. 7C-E. Each stopcock 2 is then maintained in its coupling 10, with a bearing point 14 at the front of the manifold 7, at the level of the edge of the closed hole 11;
  a latch 13, for example on a spring or automated, then bears on the rear 15 of the body of the stopcock manifold 7, which then prevents the manifold 7 from rotating, which would allow it to come out of the couplings 10. The manifold 7 is therefore strictly kept in place in the couplings 10 by means of two simple bearing points, located at the front 14 and rear 15, respectively of the device or of the stopcock manifold 7, as shown in FIG. 7E.

Advantages of the Invention

The invention in particular provides the following advantages:
  quick positioning in a single, simple and natural movement;
  simplified locking mechanism, whether passive (on spring) or active (automatically actuated):
    easier to manipulate latch device;
    easy to automate latch device;
    no risk of forgetting to actuate.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

KEY

1 Stopcock manifold body
2 Stopcock
3 Inlet/outlet coupling
4 Stopcock finger or crank pin
5 Rotary actuator coupling with open notch(es)
6 Manifold blocking latch
7 Stopcock manifold
10 Rotary actuator coupling with closed notch
11 Closed notch or "hole"
12 Open notch
13 Passive latch (spring)
14 Front bearing point
15 Rear bearing point
16 Rotation axis of the stopcock
17 Vertical axis of the rotary actuator coupling

The invention claimed is:

1. A stopcock manifold system, comprising:
a manifold comprising at least one stopcock, each stopcock comprising at least one stopcock finger;
a coupling part for each at least one stopcock, each coupling part including a closed notch configured to receive the at least one stopcock finger of a corresponding stopcock, the coupling part coupling with the corresponding stopcock by insertion of the at least one stopcock finger into the closed notch by tilting the manifold and then straightening the manifold into a straightened position until the manifold abuts on a first bearing point comprising an edge of the closed notch, each coupling part further including two open notches, each open notch arranged on either side of the closed notch; and
a latch configured to maintain the manifold in the straightened position by pressing one end of the latch on the manifold at a second bearing point.

2. The stopcock manifold system according to claim 1, wherein the latch comprises a passive latch, of the spring type.

3. The stopcock manifold system according to claim 2, wherein the passive latch comprises a tongue,
wherein the passive latch is configured to move away from its equilibrium point when the manifold, while being inserted obliquely into the closed notch of each coupling part, simultaneously pushes on an end of the passive latch, and
wherein the passive latch is configured to return to its equilibrium point once the manifold has been moved to the straightened position, in which straightened position of the manifold the passive latch blocks the manifold by abutting the manifold at the second bearing point.

4. The stopcock manifold system according to claim 1, wherein the first bearing point comprises a front bearing point.

5. The stopcock manifold system according to claim 1, wherein the second bearing point comprises a rear bearing point.

6. The stopcock manifold system according to claim 1, wherein, in the straightened position, a rotation axis of the corresponding stopcock aligns with a vertical axis of the coupling part.

7. The stopcock manifold system according to claim 1, wherein each coupling part is cylindrical, and
wherein on each coupling part the two open notches are arranged circumferentially on either side of the closed notch.

* * * * *